US008163688B2

(12) United States Patent
Zelger et al.

(10) Patent No.: US 8,163,688 B2
(45) Date of Patent: Apr. 24, 2012

(54) STORAGE-STABLE FLUORESCENT WHITENER FORMULATIONS

(75) Inventors: Josef Zelger, Riehen (CH); Serge Schroeder, Rosenau (FR)

(73) Assignee: BASF SE, Ludwigshafen (DE)

( * ) Notice: Subject to any disclaimer, the term of this patent is extended or adjusted under 35 U.S.C. 154(b) by 682 days.

(21) Appl. No.: 10/559,888

(22) PCT Filed: Jun. 2, 2004

(86) PCT No.: PCT/EP2004/050983

§ 371 (c)(1),
(2), (4) Date: Dec. 7, 2005

(87) PCT Pub. No.: WO2004/111330

PCT Pub. Date: Dec. 23, 2004

(65) Prior Publication Data

US 2007/0094814 A1 May 3, 2007

(30) Foreign Application Priority Data

Jun. 11, 2003 (EP) .................................... 03405420

(51) Int. Cl.
*C07D 403/02* (2006.01)

(52) U.S. Cl. ........ 510/324; 252/548; 252/547; 252/174; 252/135; 252/91

(58) Field of Classification Search .................. 510/324, 510/234; 252/548, 547, 91, 96, 174, 135
See application file for complete search history.

(56) References Cited

U.S. PATENT DOCUMENTS

| | | | | |
|---|---|---|---|---|
| 5,057,236 | A * | 10/1991 | Petrin et al. | 510/324 |
| 5,076,968 | A * | 12/1991 | Fringeli et al. | 510/325 |
| 5,174,927 | A * | 12/1992 | Honsa | 510/325 |
| 5,429,767 | A | 7/1995 | Zelger | 252/174.17 |
| 5,518,657 | A | 5/1996 | Fringeli et al. | 252/301.23 |
| 5,708,151 | A * | 1/1998 | Mockli | 534/608 |
| 5,714,450 | A * | 2/1998 | Brouwer | 510/324 |
| 5,945,396 | A | 8/1999 | Eckhardt et al. | 510/521 |
| 6,503,877 | B2 * | 1/2003 | Grande et al. | 510/380 |
| 6,762,287 | B2 * | 7/2004 | Mockli | 534/607 |
| 6,878,679 | B2 * | 4/2005 | Sommerville-Roberts et al. | 510/296 |
| 2003/0089888 | A1 | 5/2003 | Bacher et al. | 252/301.21 |

* cited by examiner

*Primary Examiner* — Milton I Cano
*Assistant Examiner* — Mohammad Asdjodi
(74) *Attorney, Agent, or Firm* — Sheila A. Loggins

(57) ABSTRACT

The present invention relates to a storage-stable fluorescent whitener formulation, comprising a compound of formula 1, a process for their preparation and their use.

(1)

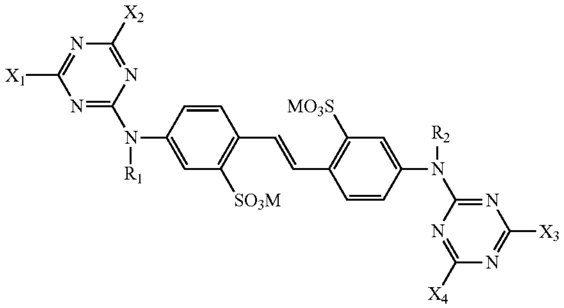

17 Claims, No Drawings

STORAGE-STABLE FLUORESCENT WHITENER FORMULATIONS

This application is a 371 of PCT/EPO4/50983, Jun. 2, 2004.

The present invention relates to storage-stable fluorescent whitener formulations, a process for their preparation and their use.

The storage-stable fluorescent whitener formulations according to the invention comprise (a) 5-60% by weight, based on the total weight of the whitener formulation, of at least one compound of formula (1)

(1)

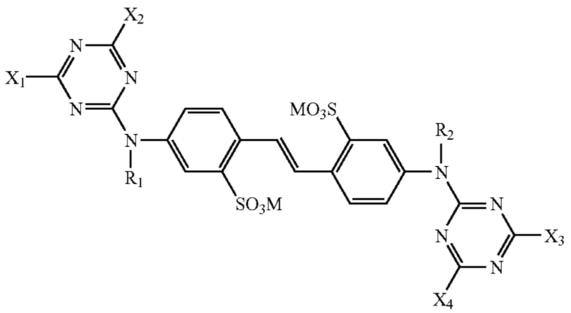

wherein $R_1$ and $R_2$ are, independently from each other, hydrogen; unsubstituted $C_1$-$C_8$alkyl or substituted $C_1$-$C_8$alkyl, $X_1$, $X_2$, $X_3$ and $X_4$ are, independently from each other, —$N(R_3)R_4$ or —$OR_5$, wherein $R_3$ and $R_4$ are, independently from each other, hydrogen; cyano; unsubstituted $C_1$-$C_8$alkyl; substituted $C_1$-$C_8$alkyl; unsubstituted $C_7$cycloalkyl or unsubstituted $C_5$-$C_7$cycloalkyl; or $R_3$ and $R_4$, together with the nitrogen atom linking them, form a heterocyclic ring, and $R_5$ is unsubstituted $C_1$-$C_8$alkyl or substituted $C_1$-$C_8$alkyl, and M is hydrogen or a cation, (b) 0.01-1% by weight, based on the total weight of the whitener formulation, of at least one anionic polysaccharide, (c) 0-25% by weight, based on the total weight of the whitener formulation, of at least one electrolyte, (d) 0-20% by weight, based on the total weight of the whitener formulation, of at least one dispersant, (e) 0-30% by weight, based on the total weight of the whitener formulation, of at least one further fluorescent whitener, (f) 0-20% by weight, based on the total weight of the whitener formulation, of at least one further optional component, and (g) water to make up 100% by weight.

These novel formulations are suspensions, and are stable for several months even at elevated temperatures.

Within the scope of the above definitions, $C_1$-$C_8$alkyl may be methyl, ethyl, n- or isopropyl, n-, sec.- or t-butyl, or linear or branched pentyl, hexyl, heptyl or octyl. Preferred are $C_1$-$C_4$alkyl groups. In case the alkyl groups are substituted examples of possible substituents are hydroxyl, halogen, like fluorine, chlorine or bromine, sulfo, sulfate, carboxy and $C_1$-$C_4$alkoxy, like methoxy and ethoxy. Other substituents of such alkyl groups are, for example, cyano, —$CONH_2$ and phenyl. Preferred substituents are hydroxy, carboxy, cyano, —COOH, $H_2NC(NH)NH_2$, —$CONH_2$ and phenyl, especially hydroxy and carboxy. Furthermore, highly preferred substituents are hydroxy and $C_1$-$C_4$alkoxy, especially hydroxy. The alkyl groups can also be uninterrupted or interrupted by —O— (in case of alkyl groups containing two or more carbon atoms).

Examples for $C_5$-$C_7$cycloalkyl groups are cyclopentyl and especially cyclohexyl. These groups can be unsubstituted or substituted by, for example, $C_1$-$C_4$-alkyl, like methyl. Preferred are the corresponding unsubstituted cycloalkyl groups.

Halogen may be fluorine, chlorine, bromine or Iodine, preferably chlorine.

If $R_3$ and $R_4$ together with the nitrogen atom form a heterocyclic ring such a ring system can be, for example, morpholino, piperidine or pyrrolidine. The heterocylic ring can be unsubstituted or substituted. An example for such substituents is $C_1$-$C_4$alkyl, especially methyl.

The cation M is preferably an alkali metal cation, an alkaline earth metal cation, ammonium or a cation formed from an amine. Preferred are Li, Na, K, Ca, Mg, ammonium, mono-, di-, tri- or tetra-$C_1$-$C_4$alkylammonium, mono-, di- or tri-$C_2$-$C_4$-hydroxyalkylammonium or ammonium that is di- or tri-substituted with a mixture of $C_1$-$C_4$-alkyl and $C_2$-$C_4$-hydroxyalkyl groups. Highly preferred is sodium.

$R_1$ and $R_2$ are preferably, independently from each other, hydrogen; unsubstituted $C_1$-$C_4$alkyl or substituted $C_1$-$C_4$alkyl, especially hydrogen.

$R_3$ and $R_4$ are preferably, independently from each other, hydrogen; cyano; $C_1$-$C_8$alkyl which is unsubstituted or substituted by hydroxy, carboxy, cyano, —COOH, —$H_2NC(NH)NH_2$—, —$CONH_2$ or phenyl, especially by hydroxy or carboxy, and wherein the $C_1$-$C_8$alkyl group is uninterrupted or interrupted by —O—; unsubstituted or $C_1$-$C_4$alkyl-substituted $C_5$-$C_7$cycloalkyl, especially cyclohexyl; or $R_3$ and $R_4$, together with the nitrogen atom linking them, form an unsubstituted morpholino, piperidine or pyrrolidine ring or a $C_1$-$C_4$alkyl-substituted morpholino, piperidine or pyrrolidine ring.

More preferably, $R_3$ and $R_4$ are, independently from each other, hydrogen; unsubstituted $C_1$-$C_8$alkyl or hydroxy-substituted $C_1$-$C_8$alkyl; unsubstituted $C_5$-$C_7$cycloalkyl or $C_1$-$C_4$alkyl-substituted CB-cycloalkyl; or $R_3$ and $R_4$, together with the nitrogen atom linking them, form an unsubstituted morpholino, piperidine or pyrrolidine ring or $C_1$-$C_4$alkyl-substituted morpholino, piperidine or pyrrolidine ring.

Most preferred meanings for $R_3$ and $R_4$ are, Independently from each other, hydrogen; unsubstituted $C_1$-$C_8$alkyl or hydroxy-unsubstituted $C_1$-$C_8$alkyl; or $R_3$ and $R_4$, together with the nitrogen atom linking them, form an unsubstituted morpholino, piperidine or pyrrolidine ring or a $C_1$-$C_4$alkyl-substituted morpholino, piperidine or pyrrolidine ring.

Highly preferred are unsubstituted morpholino, piperidine or pyrrolidine rings or a $C_1$-$C_4$alkyl-substituted morpholino, piperidine or pyrrolidine rings, especially morpholino, formed by $R_3$ and $R_4$ together with the nitrogen atom linking them.

Examples of —$N(R_3)R_4$ groups are —$NH_2$; —$NHCH_3$; —$NHC_2H_5$; —$NH(n\text{-}H_7)$; —$NH(i\text{-}C_3H_7)$; —$NH(i\text{-}C_4H_9)$; —$N(CH_3)_2$; —$N(C_2H_5)_2$; —$N(i\text{-}C_3H_7)_2$; —$NH(CH_2CH_2OH)$; —$N(CH_2CH_2OH)_2$; —$N(CH_2CH(OH)CH_3)_2$; —$N(CH_3)(CH_2CH_2OH)$; —$N(C_2H_5)(CH_2CH_2OH)$; —$N(i\text{-}C_3H_7)(CH_2CH_2CH_2OH)$; —$NH(CH_2CH(OH)CH_3)$; —$N(C_2H_5)(CH_2CH(OH)CH_3)$; —$NH(CH_2CH_2OCH_3)$; —$NH(CH_2CH_2OCH_2CH_2OH)$; —$NH(CH_2COOH)$; —$NH(CH_2CH_2COOH)$; —$N(CH_3)(CH_2COOH)$; —$NH(CN)$;

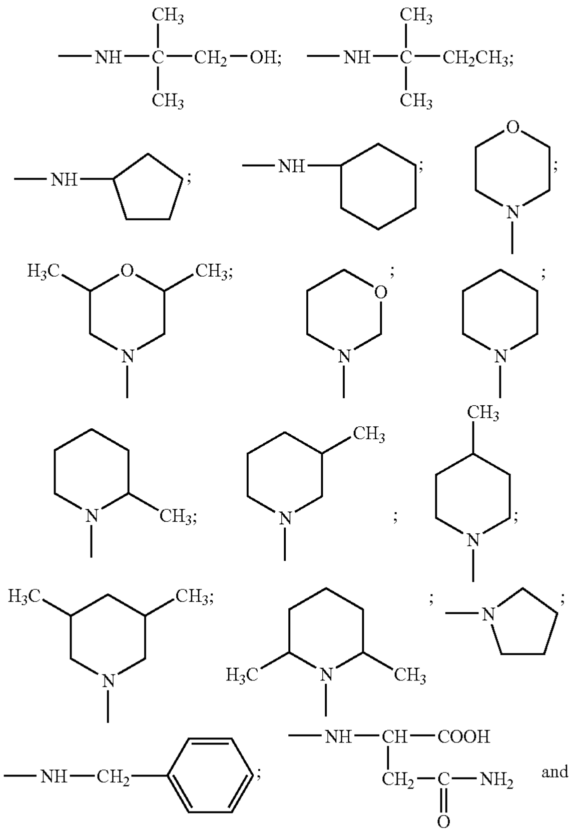

and

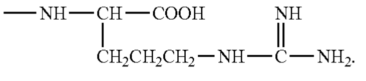

$R_5$ is preferably unsubstituted $C_1$-$C_8$alkyl or substituted $C_1$-$C_8$alkyl, especially $C_1$-$C_4$alkyl, which is unsubstituted or substituted by $C_1$-$C_4$alkoxy or especially hydroxy. Highly preferred for $R_5$ is methyl or ethyl, especially methyl.

$X_1$, $X_2$, $X_3$ and $X_4$ are preferably a radical of formula —$N(R_3)R_4$.

$X_1$ and $X_3$ have preferably the same meanings. In addition it is preferred that $X_2$ and $X_4$ have preferably the same meanings. Furthermore, it is preferred that the four radicals $X_1$, $X_2$, $X_3$ and $X_4$ do not have identical meanings.

Preferred are compounds of formula (1), wherein $R_1$ and $R_2$ are, independently from each other, hydrogen or unsubstituted $C_1$-$C_4$alkyl, each $X_1$, $X_2$, $X_3$ and $X_4$ is independently from each other a radical of formula —$N(R_3)R_4$ or $OR_5$, wherein $R_3$ and $R_4$ are, independently from each other, hydrogen; cyano; $C_1$-$C_8$alkyl which is unsubstituted or substituted by hydroxy, carboxy, COOH, cyano, —$CONH_2$, NHC(NH)$NH_2$ or phenyl and wherein the $C_1$-$C_8$alkyl group is uninterrupted or interrupted by —O—; unsubstituted $C_5$-$C_7$cycloalkyl or $C_1$-$C_4$alkyl-substituted $C_5$-$C_7$cycloalkyl; or $R_3$ and $R_4$, together with the nitrogen atom linking them, form an unsubstituted morpholino, piperidine or pyrrolidine ring or a $C_1$-$C_4$alkyl-substituted morpholino, piperidine or pyrrolidine ring; and $R_5$ is $C_1$-$C_8$alkyl which is unsubstituted or substituted by hydroxy.

Highly preferred are compounds of formula (1), wherein $R_1$ and $R_2$ are, independently from each other, hydrogen or unsubstituted $C_1$-$C_4$alkyl, $X_1$ and $X_3$ are —$NH_2$, and $X_2$ and $X_4$ are a radical of formula —$N(R_3)R_4$, wherein $R_3$ and $R_4$ are, independently from each other, hydrogen; cyano; $C_1$-$C_8$alkyl which is unsubstituted or substituted hydroxy, carboxy, —COOH, cyano, —$CONH_2$, NHC(NH)$NH_2$ or phenyl, and wherein the $C_1$-$C_8$alkyl group is uninterrupted or interrupted by —O—; unsubstituted cyclohexyl or $C_1$-$C_4$alkyl-substituted cyclohexyl; unsubstituted cyclopentyl or $C_1$-$C_4$alkyl-substituted cyclopentyl or $R_3$ and $R_4$, together with the nitrogen atom linking them, form an unsubstituted morpholino, piperidine or pyrrolidine ring or a $C_1$-$C_4$alkyl-substituted morpholino, piperidine or pyrrolidine ring.

Of particular interest are compounds of formula (1), wherein $R_1$ and $R_2$ are, independently from each other, hydrogen or unsubstituted $C_1$-$C_2$alkyl, $X_1$ and $X_3$ are —$NH_2$, and $X_2$ and $X_4$ are a radical of formula —$N(R_3)R_4$, wherein $R_3$ and $R_4$ are, independently of each other, hydrogen; unsubstituted $C_1$-$C_8$alkyl or hydroxy-substituted $C_1$-$C_8$alkyl; unsubstituted cyclopentyl or $C_1$-$C_4$alkyl-substituted cyclopentyl or cyclohexyl; unsubstituted or $C_1$-$C_4$alkyl-substituted cyclohexyl; or $R_3$ and $R_4$, together with the nitrogen atom linking them, form an unsubstituted morpholino, piperidine or pyrrolidine ring or a $C_1$-$C_4$alkyl-substituted morpholino, piperidine or pyrrolidine ring.

Most interesting compounds of formula (1) are those wherein $R_3$ and $R_4$, together with the nitrogen atom linking them, form an unsubstituted morpholino, piperidine or pyrrolidine ring or a $C_1$-$C_4$alkyl-substituted morpholino, piperidine or pyrrolidine ring.

The amount of the compound(s) of formula (1) is from 5 to 60% by weight, preferably 5 to 50% by weight, more preferably 10 to 50% by weight, most preferably 10 to 45% by weight, based on the total weight of the whitener formulation.

The compounds of formulae (1) are known or can be prepared in analogy to known processes.

Compounds of formula (1) may be produced by reacting, under known reaction conditions, cyanuric chloride, successively, in any desired sequence, with each of 4,4'-diaminostilbene-2,2'-disulfonic acid, and amino compounds capable of introducing the groups $X_1$, $X_2$, $X_3$ and $X_4$. Preferably, 2 moles of cyanuric chloride are initially reacted with 1 mole of 4,4'-diaminostilbene-2,2'-disulfonic acid and then reacting the intermediate obtained in any order with amino compounds capable of introducing the groups $X_1$, $X_2$, $X_3$ and $X_4$. For the preparation of compounds wherein $X_1$ and $X_3$ having the same meaning, and also $X_2$ and $X_4$ have the same meaning, it is preferred to react the intermediate obtained first with an amino compound capable of introducing $X_1$ and $X_3$, and, finally with an amino compound capable of introducing $X_2$ and $X_4$. It is also possible to carry out the reaction with the amino compounds in one step by reacting the intermediate with a mixture of amino compounds; in such a case usually corresponding mixtures of compounds of formula (1) are obtained.

Compounds of formula (1) containing a radical of formula —ON can for example be prepared by first reacting cyanuric chloride with the corresponding alcohol HORN, reacting the product obtained with 4,4'-diaminostilbene-2,2'-disulfonic acid and then reacting the intermediate with further compounds capable of introducing the remaining groups of $X_1$, $X_2$, $X_3$ and $X_4$. The last reaction is preferably carried out with the corresponding amines.

The content of dispersant is 0 to 20% by weight, based on the total weight of the whitener formulation, preferably 0.1 to 20% by weight, more preferably 0.1 to 10% by weight, most preferably 0.2 to 5% by weight.

The storage-stable fluorescent whitener formulations according to the invention can further comprise 0-30% by weight, based on the total weight of the whitener formulation, of at least one further fluorescent whitener of formula (2)

(2)

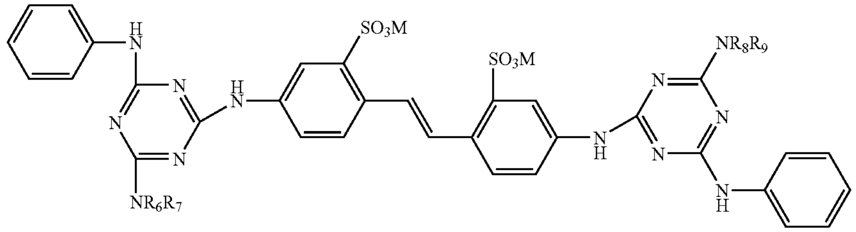

The anionic polysaccharides which can be used according to the invention belong to the group of modified polysaccharides which can be derived from cellulose, starch or the heteropolysaccharides, it being possible for the side chains to contain further monosaccharides, for example mannose and glucuronic acid. Examples of anionic polysaccharides are sodium alginate, carboxymethylated guar, carboxymethylcellulose, carboxymethyl-starch, carboxymethylated locust bean flour and, particularly preferably, xanthan gum.

The amount of polysaccharide is 0.01 to 1% by weight, a range from 0.05 to 0.5% by weight being preferred and a range of 0.1 to 0.3% by weight being particularly preferred, in each case based on the total weight of the whitener formulation. However, these ranges can be exceeded in formulations of very high concentration or very low concentration.

One or more alkali metal salts and salts of lower carboxylic acids, for example, can be used as the electrolyte. Examples of electrolytes are sodium chloride, sodium sulfate, sodium phosphate, sodium carbonate, sodium formate, sodium citrate or one of the corresponding potassium salts, and mixtures of these electrolytes. Sodium chloride, sodium citrate and the formates are preferred here. The amount of electrolyte can be 0 to 25% by weight, preferably 0.5 to 20% by weight and most preferably 0.5 to 15% by weight, based on the total weight of the whitener formulation.

Dispersants which can be used are those of the anionic or nonionic type. Examples of these are alkylbenzenesulfonates, alkyl or alkenyl ether-sulfonate salts, saturated or unsaturated fatty acids, alkyl or alkylene ether-carboxylic salts, sulfo-fatty acid salts or esters, phosphate esters, polyoxyethylene alkyl or alkenyl ethers, polyoxyethylene alkylvinyl ethers, polyoxypropylene alkyl or alkenyl ethers, polyoxybutylene alkyl or alkenyl ethers, higher fatty acid alkanolamides or alkylene oxide adducts, sucrose/fatty acid esters, fatty acid/glycol monoesters, alkylamine oxides and condensation products of aromatic sulfonic acids with formaldehyde, and lignin-sulfonates, or mixtures of the abovementioned dispersants. The condensation products of aromatic sulfonic acids with formaldehyde, and lignin-sulfonates are preferred. Condensation products of naphthalenesulfonic acids with formaldehyde and of ditolyl ether-sulfonic acids with formaldehyde are particularly preferred.

wherein $R_6$ and $R_8$, independently from each other, are hydrogen; unsubstituted $C_1$-$C_8$alkyl or substituted $C_1$-$C_8$alkyl, $R_7$ and $R_9$, independently from each other, are hydrogen; unsubstituted phenyl; unsubstituted $C_1$-$C_8$alkyl or substituted $C_1$-$C_8$alkyl, or $NR_6R_7$ and/or $NR_8R_9$ form a morpholino ring, and M is hydrogen or a cation, and/or of at least one further fluorescent whitener of formula (3)

(3)

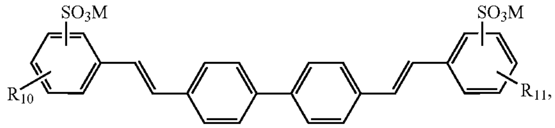

wherein $R_{10}$ and $R_{11}$, independently from each other, are hydrogen; substituted $C_1$-$C_8$alkyl or unsubstituted $C_1$-$C_8$alkyl; $C_1$-$C_8$alkoxy or halogen, and M is hydrogen or a cation.

Preferred compounds of formula (2) are those wherein $R_6$ and $R_8$, independently from each other, are hydrogen; unsubstituted $C_1$-$C_4$alkyl or substituted $C_1$-$C_4$alkyl, $R_7$ and $R_9$, independently from each other, are unsubstituted phenyl; unsubstituted $C_1$-$C_4$alkyl or substituted $C_1$-$C_4$alkyl, or $NR_6R_7$ and/or $NR_8R_9$ form a morpholino ring, and M is an alkali metal atom, an alkaline earth metal atom, ammonium or a cation formed from an amine.

More preferred compounds of formula (2) are those wherein $R_6$ and $R_8$, independently from each other, are hydrogen; unsubstituted $C_1$-$C_2$alkyl or $C_1$-$C_4$alkyl, which is substituted by hydroxy or $C_1$-$C_4$alkoxy, $R_7$ and $R_9$, independently from each other, are unsubstituted phenyl; unsubstituted $C_1$-$C_2$alkyl or $C_1$-$C_4$alkyl, which is substituted by hydroxy or $C_1$-$C_4$alkoxy, or $NR_6R_7$ and/or $NR_8R_9$ form a morpholino ring, and M is an alkali metal atom.

Especially preferred compounds of formula (2) are those of formula (2a)

(2a)

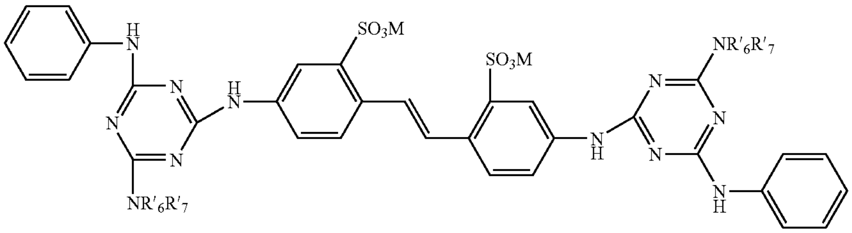

wherein $R'_6$ is hydrogen; unsubstituted $C_1$-$C_2$alkyl or $C_1$-$C_4$alkyl, which is substituted by hydroxy or $C_1$-$C_4$alkoxy, $R'_7$ is unsubstituted phenyl; unsubstituted $C_1$-$C_2$alkyl or $C_1$-$C_4$alkyl, which is substituted by hydroxy or $C_1$-$C_4$alkoxy, or $NR'_6R'_7$ forms a morpholino ring, and M is an alkali metal atom, preferably sodium.

Example of such preferred compounds of formula (2) are those of formula (2b)-(2f)

(2b)

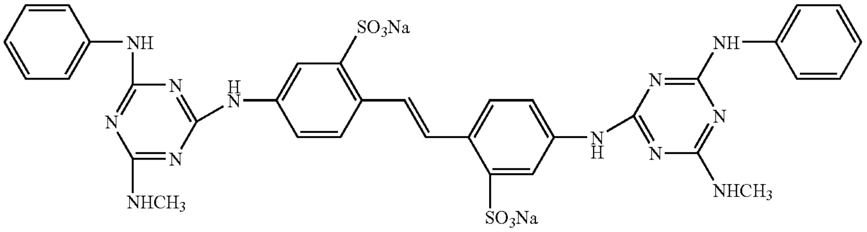

, (2c)

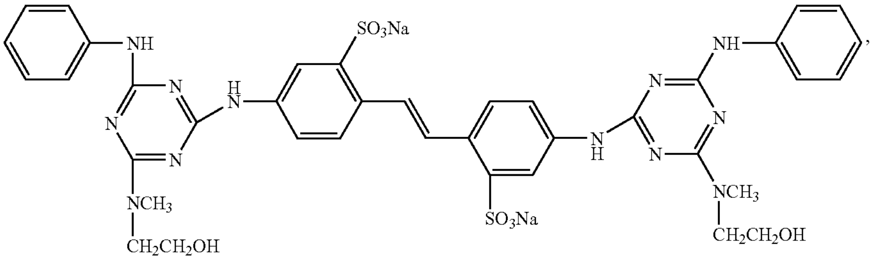

, (2d)

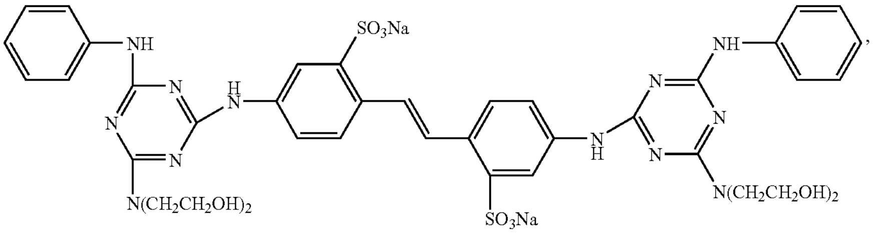

, (2e)

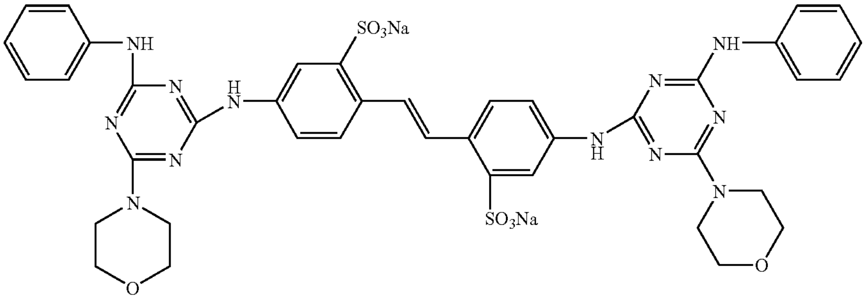

and

-continued (2f)

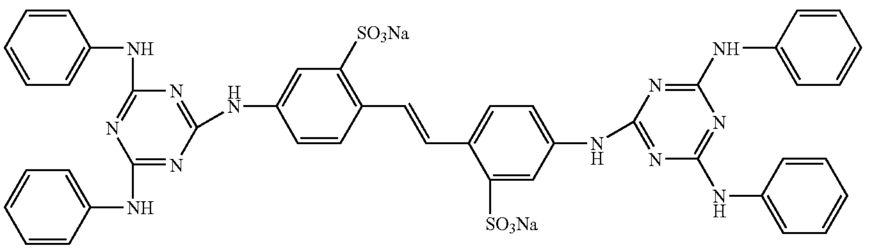

Preferred compounds of formula (3) are those wherein $R_{10}$ and $R_{11}$, independently from each other, are hydrogen; unsubstituted $C_1$-$C_4$alkyl or substituted $C_1$-$C_4$alkyl; $C_1$-$C_4$alkoxy or halogen, and M is hydrogen or a cation.

Compounds of formula (2) and (3) as well as their process of production are known.

In the mixtures of compounds of formulae (1) and (2) and/or (3) the molar ratio of compound (1) to compound (2) and/or compound (3) is usually in the range of from 0.1:99.9 to 99.9:0.1, preferably from 1:99 to 99:1 and more preferably from 5:95 to 95:5. Highly preferred is a molar ratio of from 10:90 to 90:10, especially 20:80 to 80:20. Most important is a molar ratio of from 30:70 to 70:30, especially 40:60 to 60:40.

The content of the further fluorescent whitener(s) is 0-30% by weight, based on the total weight of the whitener formulation, preferably 0 to 25% by weight, more preferably 0 to 20% by weight.

If appropriate, the whitener formulation according to the invention can further comprise optional components; examples are preservatives or mixtures of preservatives, such as chloroacetamide, triazine derivates, benzoisothiazolines, 2-methyl-2H-isothiazol-3 on, 2-octyl-2H-isothiazol-3on, 2-brom-2-nitropropan-1,3-diol or aqueous formaldehyde solution; Mg/Al silicates or mixtures of Mg/Al silicates, such as bentonite, montmorillonite, zeolites or highly disperse silicic acids; odour improvers and perfuming agent or mixtures thereof; antifoam agents or mixtures thereof; builders or mixtures thereof; protective colloids or mixtures thereof; stabilizers or mixtures thereof, sequestering agents and antifreeze agents or mixtures thereof, such as propylene glycol.

The content of these optional components is 0 to 20% by weight, based on the total weight of the whitener formulation, preferably 0.1 to 20% by weight, more preferably 0.1 to 10% by weight, most preferably 0.2 to 5% by weight.

Examples of suitable builders or protective colloids are modified polysaccharides derived from cellulose or heteropolysaccharides, such as xanthan gum, carboxymethylcellulose and polyvinyl alcohols (PVA), polyvinylpyrrolidones (PVP), polyethylene glycols (PEG) and aluminium silicates or magnesium silicates. They are usually used in a concentration range of 0.01 to 2% by weight and preferably 0.05 to 0.5% by weight, based on the total weight of the whitener formulation.

Examples of auxiliaries which can be used for stabilization are ethylene glycol, propylene glycol or dispersants in an amount of 0.2 to 5% by weight and preferably 0.3 to 2% by weight, based on the total weight of the whitener formulation.

Compounds which are used as preservatives are chloroacetamide, triazine derivates, benzoisothiazolines, 2-methyl-2H-isothiazol-3 on, 2-octyl-2H-isothiazol-3 on, 2-brom-2-nitropropan-1,3-diol or aqueous formaldehyde solution in an amount of 0.1 to 1% by weight and preferably 0.1 to 0.5% by weight based on the total weight of the whitener formulation.

A preferred storage-stable fluorescent whitener formulation according to the invention comprises (a) 6-50% by weight, preferably 10-50% by weight, more preferably 10-45% by weight, based on the total weight of the whitener formulation, of at least one compound of formula (1')

(1')

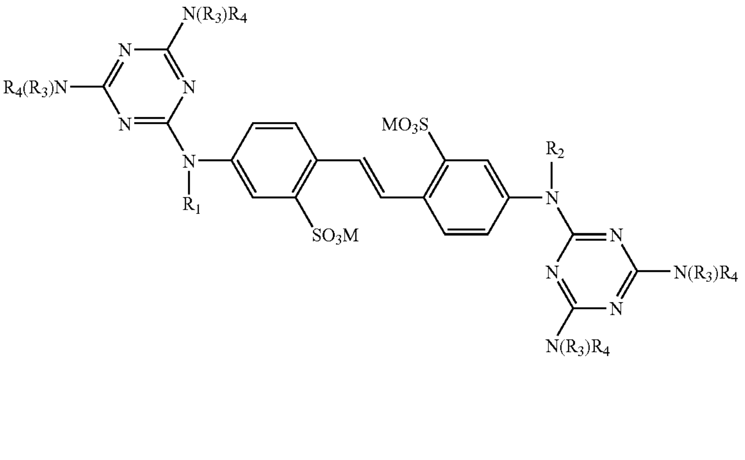

wherein $R_1$ and $R_2$ are, independently from each other, hydrogen or unsubstituted $C_1$-$C_4$alkyl, $R_3$ and $R_4$ are, independently from each other, hydrogen; cyano; $C_1$-$C_8$alkyl which is unsubstituted or substituted by hydroxy, carboxy, —COOH, —$H_2NC(NH)NH_2$, cyano, —$CONH_2$ or phenyl and wherein the $C_1$-$C_8$alkyl group is uninterrupted or interrupted by —O—; unsubstituted $C_5$-$C_7$cycloalkyl or $C_1$-$C_4$alkyl-substituted $C_5$-$C_7$cycloalkyl; or $R_3$ and $R_4$, together with the nitrogen atom linking them, form an unsubstituted morpholino, piperidine or pyrrolidine ring or a $C_1$-$C_4$alkyl-substituted morpholino, piperidine or pyrrolidine ring; and M is an alkali metal cation; an alkaline earth metal cation; ammonium or a cation formed from an amine, (b) 0.05-0.5% by weight, preferably 0.1-0.3% by weight, based on the total weight of the whitener formulation, of at least one anionic polysaccharide, (c) 0-25% by weight, preferably 0.5-20% by weight, more preferably 0.5-15% by weight, based on the total weight of the whitener formulation, of at least one electrolyte from the group consisting of alkali metal salts and/or lower carboxylic acids, (d) 0-20% by weight, preferably 0.1-20% by weight, more preferably, 0.1-10% by weight, especially preferred 0.2-5% by weight, based on the total weight of the whitener formulation, of at least one dispersant from the group consisting of alkylbenzenesulfonates; alkyl or alkenyl ethersulfonate salts; saturated or unsaturated fatty adds; alkyl or alkylene ether-carboxylic salts; sulfo-fatty acid salts or esters; phosphate esters; polyoxyethylene alkyl or alkenyl ethers; polyoxyethylene alkylvinyl ethers; polyoxypropylene alkyl or alkenyl ethers; polyoxybutylene alkyl or alkenyl ethers; higher fatty acid alkanolamides or alkylene oxide adducts; sucrose/fatty acid esters; fatty acid/glycol monoesters; alkylamine oxides and condensation products of aromatic sulfonic acids with formaldehyde; and ligninsulfonates, (e) 0-30% by weight, preferably 0-25% by weight, more preferably 0-20% by weight, based on the total weight of the whitener formulation, of at least one further fluorescent whitener from the group consisting of compounds of formula (2)

(2)

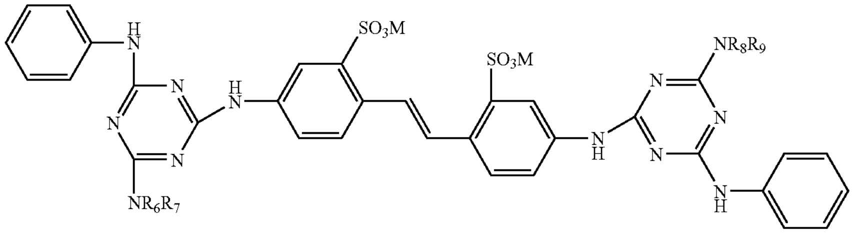

wherein $R_6$ and $R_8$, independently from each other, are hydrogen; unsubstituted $C_1$-$C_2$alkyl or $C_1$-$C_4$alkyl, which is substituted by hydroxy or $C_1$-$C_4$alkoxy, $R_7$ and $R_9$, Independently from each other, are unsubstituted phenyl; unsubstituted $C_1$-$C_2$alkyl or $C_1$-$C_4$alkyl, which is substituted by hydroxy or $C_1$-$C_4$alkoxy, or $NR_6R_7$ and/or $NR_8R_9$ form a morpholino ring, and M is an alkali metal atom, and compounds of formula (3)

(3)

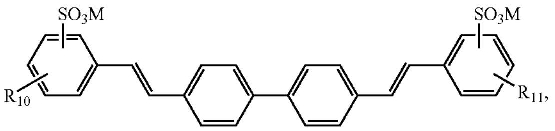

wherein $R_{10}$ and $R_{11}$, independently from each other, are hydrogen; $C_1$-$C_4$alkyl; $C_1$-$C_4$alkoxy or halogen, and M is hydrogen or a cation, (f) 0-20% by weight, preferably 0.1 to 20% by weight, more preferably 0.1 to 10% by weight, most preferably 0.2 to 5% by weight based on the total weight of the whitener formulation, of at least one further optional component from the group consisting of preservatives; Mg/Al silicates; odour improvers and perfuming agent; builder or protective colloids; stabilizers; sequestering agents and antifreeze agents, (g) water to make up 100% by weight.

A more preferred storage-stable fluorescent whitener formulations according to the invention comprises (a) 10-50% by weight, preferably 10-45% by weight, based on the total weight of the whitener formulation, of at least one compound of formula (1")

(1″)

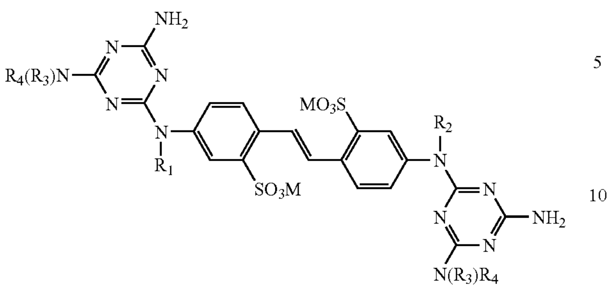

wherein $R_1$ and $R_2$ are, independently from each other, hydrogen; methyl or ethyl, $R_3$ and $R_4$ are, independently from each other, hydrogen; cyano; $C_1$-$C_8$alkyl which is unsubstituted or substituted by hydroxy, carboxy, —COOH, —$CONH_2$, $H_2NC(NH)NH_2$, phenyl and wherein the $C_1$-$C_8$alkyl group is uninterrupted or interrupted by —O—; unsubstituted $C_5$-$C_7$cyclohexyl or $C_1$-$C_4$alkyl-substituted $C_5$-$C_7$cyclohexyl; or $R_3$ and $R_4$, together with the nitrogen atom linking them, form an unsubstituted morpholino, piperidine or pyrrolidine ring or a $C_1$-$C_4$alkyl-substituted morpholino, piperidine or pyrrolidine ring; and M is Li; Na; Ca; Mg; ammonium; mono-, di-, tri- or tetra-$C_1$-$C_4$alkylammonium; mono-, di- or tri-$C_2$-$C_4$-hydroxyalkylammonium or ammonium that is di- or tri-substituted with a mixture of $C_1$-$C_4$-alkyl and $C_2$-$C_4$-hydroxyalkyl groups, (b) 0.05-0.5% by weight, preferably 0.1-0.3% by weight, based on the total weight of the whitener formulation, of at least one anionic polysaccharide from the group consisting of sodium alginate; carboxymethylated guar; carboxymethylcellulose; carboxymethyl-starch; carboxymethylated locust bean flour and xanthan gum, (c) 0-25% by weight, preferably 0.5-20% by weight, more preferably 0.5-15% by weight, based on the total weight of the whitener formulation, of at least one electrolyte from the group consisting of sodium or potassium chloride; sodium or potassium sulfate; sodium or potassium phosphate; sodium or potassium carbonate; sodium or potassium formate; sodium or potassium citrate, (d) 0-20% by weight, preferably 0.1-20% by weight, more preferably, 0.1-10% by weight, especially preferred 0.2-5% by weight, based on the total weight of the whitener formulation, of at least one dispersant from the group consisting of alkylbenzenesulfonates; alkyl or alkenyl ether-sulfonate salts; saturated or unsaturated fatty acids; alkyl or alkylene ether-carboxylic salts; sulfo-fatty acid salts or esters; phosphate esters; polyoxyethylene alkyl or alkenyl ethers; polyoxyethylene alkylvinyl ethers; polyoxypropylene alkyl or alkenyl ethers; polyoxybutylene alkyl or alkenyl ethers; higher fatty acid alkanolamides or alkylene oxide adducts; sucrose/fatty acid esters; fatty acid/glycol monoesters; alkylamine oxides and condensation products of naphthalene sulfonic acids with formaldehyde; and lignin-sulfonates, (e) 0-25% by weight, more preferably 0-20% by weight, based on the total weight of the whitener formulation, of at least one further fluorescent whitener from the group consisting of compounds of formula (2a)

(2a)

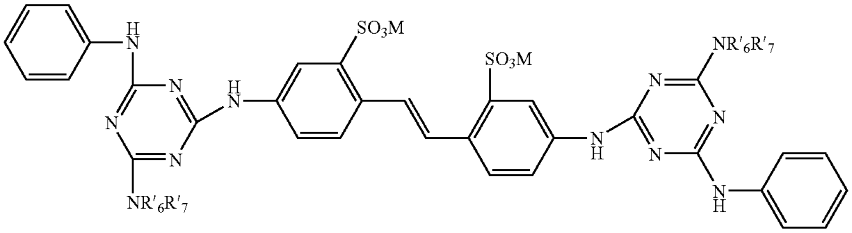

wherein $R'_6$ is hydrogen; unsubstituted $C_1$-$C_2$alkyl or $C_1$-$C_4$alkyl, which is substituted by hydroxy or $C_1$-$C_4$alkoxy, $R'_7$ is unsubstituted phenyl; unsubstituted $C_1$-$C_2$alkyl or $C_1$-$C_4$alkyl, which is substituted by hydroxy or $C_1$-$C_4$alkoxy, or $NR'_6R'_7$ forms a morpholino ring, and M is an alkali metal atom, preferably sodium, and compounds of formula (3)

(3)

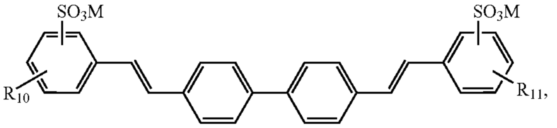

wherein $R_{10}$ and $R_{11}$, independently from each other, are hydrogen; $C_1$-$C_2$alkyl; $C_1$-$C_2$alkoxy; Cl or Br, and M is hydrogen or an alkali metal atom, preferably sodium, (f) 0-20% by weight, preferably 0.1 to 20% by weight, more preferably 0.1 to 10% by weight, particularly preferably 0.2 to 5% by weight based on the total weight of the whitener formulation, of at least one further optional component from the group consisting of chloroacetamide; triazine derivates; benzoisothiazolines; 2-methyl-2H-isothiazol-3on; 2-octyl-2H-isothiazol-3 on; 2-brom-2-nitropropan-1,3-diol; aqueous formaldehyde solution; bentonite; montmorillonite; zeolites; polyvinyl alcohols (PVA), polyvinylpyrrolidones (PVP), polyethylene glycols (PEG); aluminium silicates; magnesium silicates; ethylene glycol and propylene glycol, (g) water to make up 100% by weight.

An especially preferred storage-stable fluorescent whitener formulation according to the invention comprises (a) 10-45% by weight, based on the total weight of the whitener formulation, of at least one compound of formula (1")

(1")

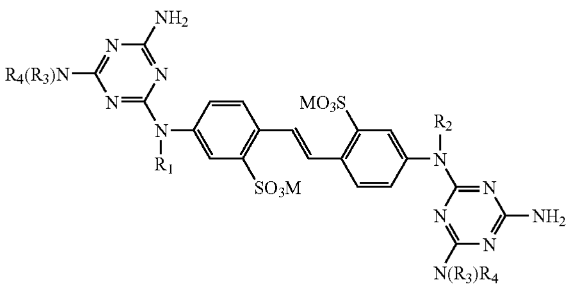

wherein $R_1$ and $R_2$ are, Independently from each other, hydrogen; methyl or ethyl, $R_3$ and $R_4$ are, independently from each other, —$NH_2$; —$NHCH_3$; —$NHC_2H_5$; —$NH(n\text{-}C_3H_7)$; —$NH(i\text{-}C_3H_7)$; —$NH(i\text{-}C_4H_9)$; —$N(CH_3)_2$; —$N(C_2H_5)_2$; —$N(i\text{-}C_3H_7)$; —$NH(CH_2CH_2OH)$; —$N(CH_2CH_2OH)_2$; —$N(CH_2CH(OH)CH_3)_2$; —$N(CH_3)(CH_2CH_2OH)$; —$N(C_2H_5)(CH_2CH_2OH)$; —$N(i\text{-}C_3H_7)(CH_2CH_2CH_2OH)$; —$NH(CH_2CH(OH)CH_3)$; —$N(C_2H_5)(CH_2CH(OH)CH_3)$; —$NH(CH_2CH_2OCH_3)$; —$NH(CH_2CH_2OCH_2CH_2OH)$; —$NH(CH_2COOH)$; —$NH(CH_2CH_2COOH)$; —$N(CH_3)(CH_2COOH)$; —$NH(CN)$;

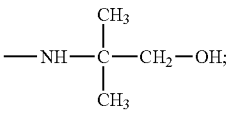
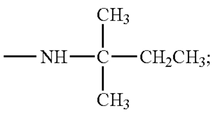

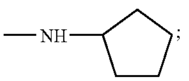
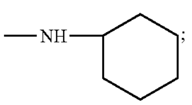
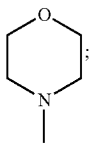

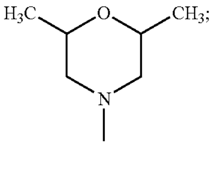
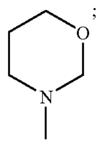
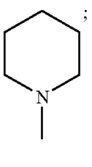

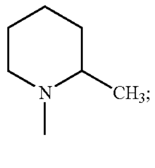
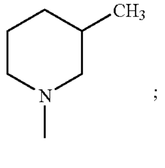
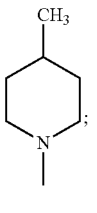

-continued

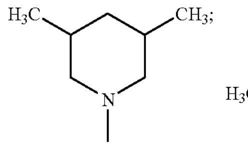
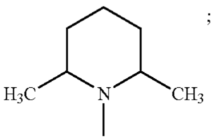
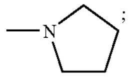

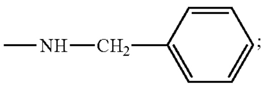
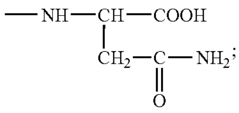
and

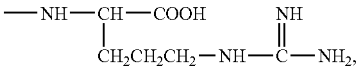

M is Li; Na; Ca; Mg; ammonium; mono-, di-, tri- or tetra-$C_1$-$C_4$alkylammonium; mono-, di- or tri-$C_2$-$C_4$-hydroxyalkylammonium or ammonium that is di- or tri-substituted with a mixture of $C_1$-$C_4$alkyl and $C_2$-$C_4$-hydroxyalkyl groups, (b) 0.05-0.5% by weight, preferably 0.1-0.3% by weight, based on the total weight of the whitener formulation, of at least one anionic polysaccharide from the group consisting of sodium alginate; carboxymethylated guar, carboxymethylcellulose; carboxymethyl-starch; carboxymethylated locust bean flour and xanthan gum, (c) 0-25% by weight, preferably 0.5-20% by weight, more preferably 0.5-15% by weight, based on the total weight of the whitener formulation, of at least one electrolyte from the group consisting of sodium or potassium chloride; sodium or potassium sulfate; sodium or potassium phosphate; sodium or potassium carbonate; sodium or potassium formate; sodium or potassium citrate, (d) 0-20% by weight, preferably 0.1-20% by weight, more preferably, 0.1-10% by weight, most preferably 0.2-5% by weight based on the total weight of the whitener formulation, of at least one dispersant from the group consisting of alkylbenzenesulfonates; alkyl or alkenyl ether-sulfonate salts; saturated or unsaturated fatty acids; alkyl or alkylene ether-carboxylic salts; sulfo-fatty acid salts or esters; phosphate esters; polyoxyethylene alkyl or alkenyl ethers; polyoxyethylene alkylvinyl ethers; polyoxypropylene alkyl or alkenyl ethers; polyoxybutylene alkyl or alkenyl ethers; higher fatty acid alkanolamides or alkylene oxide adducts; sucrose/fatty acid esters; fatty acid/glycol monoesters; alkylamine oxides and condensation products of naphthalene sulfonic acids with formaldehyde; and lignin-sulfonates, (e) 0-25% by weight, more preferably 0-20% by weight, based on the total weight of the whitener formulation, of at least one further fluorescent whitener from the group consisting of compounds of formula (2b)
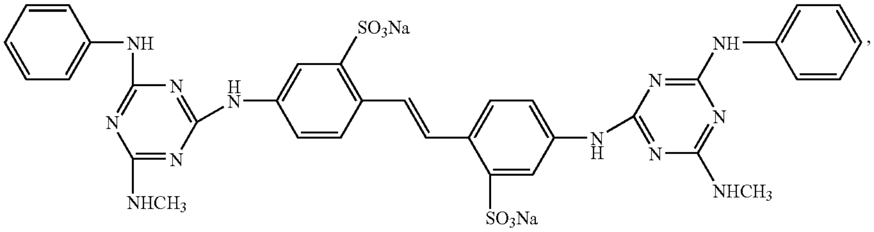
,
(2c)
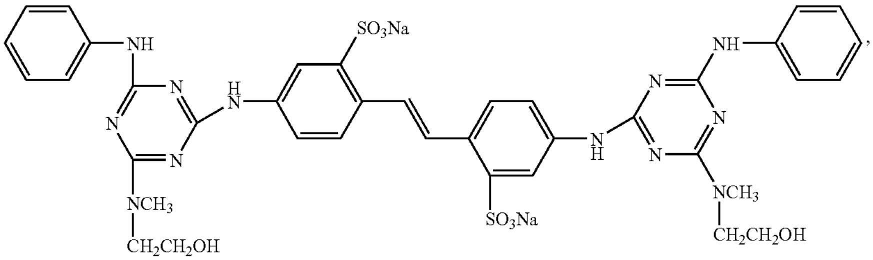
,
(2d)
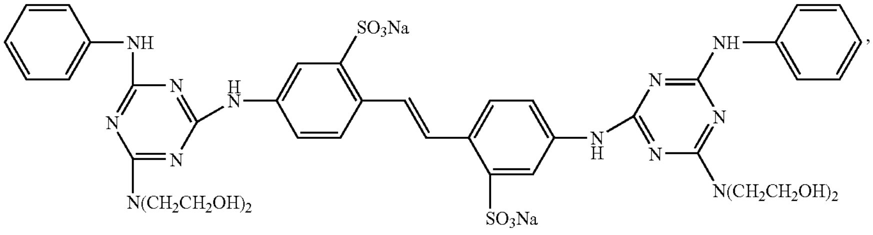
,
(2e)
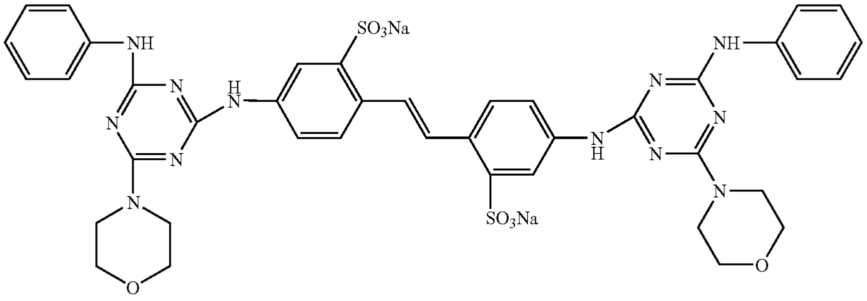
and
(2f)
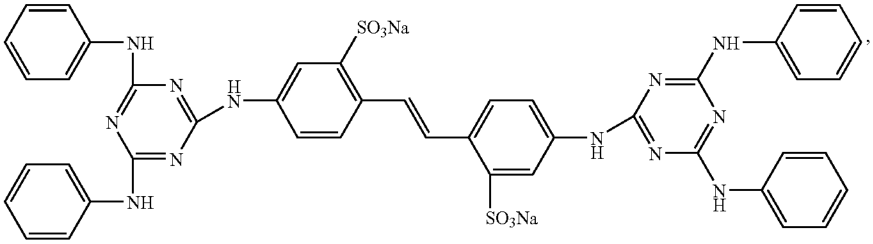
, and compounds of formula (3')

(3')

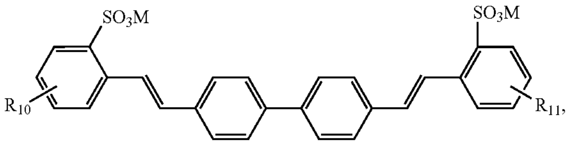

wherein $R_{10}$ and $R_{11}$, independently from each other, are hydrogen; $C_1$-$C_2$alkyl; $C_1$-$C_2$alkoxy; Cl or Br, and M is hydrogen or an alkali metal atom, preferably sodium, (f) 0-20% by weight, preferably 0.1 to 20% by weight, more preferably 0.1 to 10% by weight, particularly preferably 0.2 to 5% by weight based on the total weight of the whitener formulation, of at least one further optional component from the group consisting of chloroacetamide; triazine derivates; benzoisothiazolines; 2-methyl-2H-Isothiazol-3on; 2-octyl-2H-isothiazol-3on; 2-brom-2-nitropropan-1,3-diol; aqueous formaldehyde solution; bentonite; montmorillonite; zeolites; polyvinyl alcohols (PVA), polyvinylpyrrolidones (PVP), polyethylene glycols (PEG); aluminium silicates; magnesium silicates; ethylene glycol and propylene glycol, (g) water to make up 100% by weight.

The storage-stable formulations of this invention are prepared by mixing the moist filter cake or also the dry powder, The concentrated formulation thus prepared can be used for the fluorescent whitening of paper or textile material, for example in detergents. To this end, they are in general diluted to the optimum concentration for the practical application by the addition of further components or water.

The novel storage-stable fluorescent whitener formulations are used in particular for incorporation into washing agents, for example by allowing the required amount of the fluorescent whitener formulation according to the invention to run from a tank into a mixing device which contains a suspension of the washing agent or the dispersant.

It is also possible to prepare a solid form of the formulation according to the present invention. Such a solid formulation can be prepared according to conventional methods, such as for example spray drying.

The present invention accordingly also relates to a process for the preparation of solid and liquid washing agents, and to the washing agents obtained by this process, which comprises mixing, for example, a suspension of detergents customary for washing agents with a suspension, according to the invention, of whiteners, and drying the mixture. The drying procedure here can be carried out by, for example, a spray-drying method.

The following examples illustrate the invention, without limiting it thereto. Percentage data relate to the total weight of the formulation.

EXAMPLE 1

With stirring, the components listed below are mixed and homogenised at 20° C., 30.0% by weight of the fluorescent whitening agent of formula

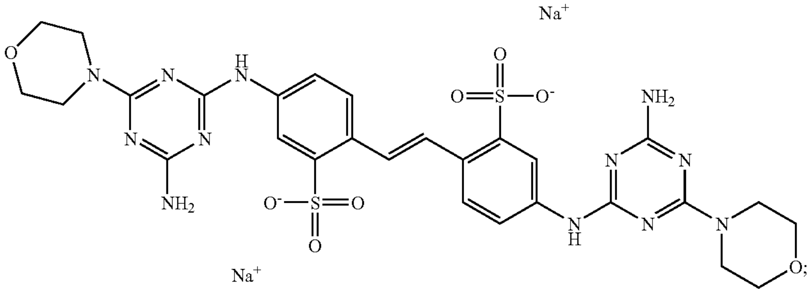

;

which comprises at least one fluorescent whitening agent of formula (1) In an amount of 5-60% by weight, based on the total weight of the formulation, with 0.01-1% by weight of an anionic polysaccharide and water, and homogenising the formulations.

The desired content of anionic fluorescent whitening agent in the suspension can be adjusted either by addition of water, aqueous electrolyte, suspension, further fluorescent agent(s) of formulae (2) and/or (3) or further dry powder to the moist filter cake. This adjustment can be made before, during or after addition of the anionic polysaccharide.

0.5% by weight of propylene glycol;

0.25% by weight of Xanthan, 0.4% by weight of Acticide MBS® (Trade name of Acti-Chem Specialties Inc.) and deionised water to make up 100%.

EXAMPLE 2

With stirring, the components listed below are mixed and homogenised at 20° C., 11.1% by weight of the fluorescent whitening agent of formula

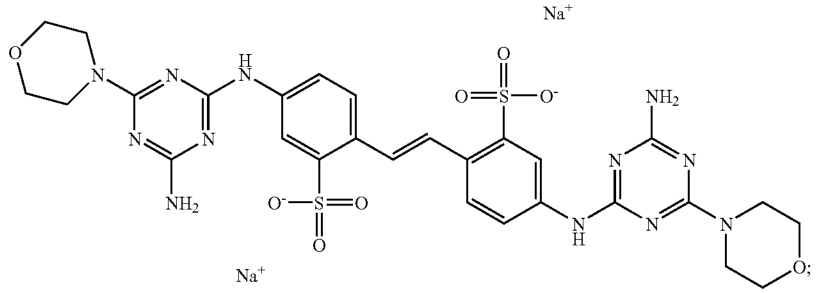

18.9% by weight of the fluorescent whitening agent of formula

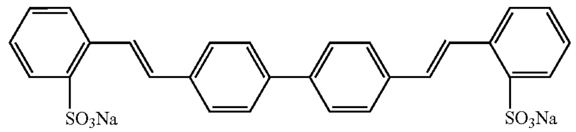

0.5% by weight of propylene glycol;

0.25% by weight of Xanthan, 0.4% by weight of Acticide MBS® (Trade name of Acti-Chem Specialties Inc.)

0.001% by weight of Surfynol 104 PG 50 ® (Trade name of Air Products and Chemicals Inc.) and deionised water to make up 100%.

The invention claimed is:

1. A storage-stable aqueous fluorescent whitener formulation consisting essentially of (a) 10%-60% by weight, based on the total weight of the whitener formulation, of at least one compound of formula (1)

(1)

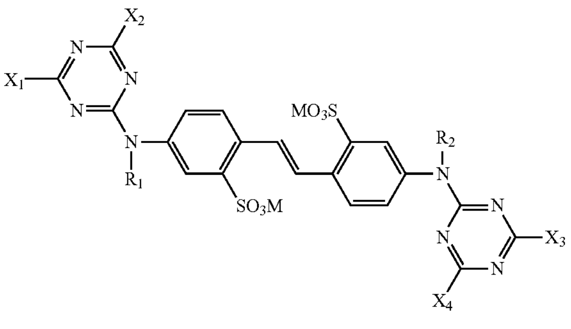

wherein $R_1$ and $R_2$ are, independently from each other, hydrogen; unsubstituted $C_1$-$C_8$alkyl or substituted $C_1$-$C_8$alkyl, $X_1$ and $X_3$ are —$NH_2$, $X_2$ and $X_4$ are, independently from each other, —$N(R_3)R_4$ or —$OR_5$, wherein $R_3$ and $R_4$ are, independently of each other, hydrogen; cyano; unsubstituted $C_1$-$C_8$alkyl; substituted $C_1$-$C_8$alkyl; unsubstituted $C_8$-$C_7$cycloalkyl or unsubstituted $C_8$-$C_7$cycloalkyl; or $R_3$ and $R_4$, together with the nitrogen atom linking them, form a heterocyclic ring, and $R_5$ is unsubstituted $C_1$-$C_8$alkyl or substituted $C_1$-$C_8$alkyl, and M is hydrogen or a cation selected from the group consisting of Li, Na, K, Ca, Mg, ammonium, mono-, di, tri or tetra $C_1$-$C_4$ alkylammonium, and mono, di- or tri-$C_2$-$C_4$-hydroxyalkylammoniuim, (b) 0.01-1% by weight, based on the total weight of the whitener formulation, of at least one anionic polysaccharide, (c) 0-25% by weight, based on the total weight of the whitener formulation, of at least one electrolyte, (d) 0-20% by weight, based on the total weight of the whitener formulation, of at least one dispersant, (e) 0-30% by weight, based on the total weight of the whitener formulation, of at least one further fluorescent whitener, (f) 0-20% by weight, based on the total weight of the whitener formulation, of at least one further optional component, and (g) water to make up 100% by weight.

2. A storage-stable fluorescent whitener formulation according to claim 1 comprising 10%-60% by weight, based on the total weight of the whitener formulation, of at least one compound of formula (1), wherein $R_1$ and $R_2$, independently from each other, hydrogen or $C_1$-$C_4$alkyl, $X_2$, and $X_4$ are independently from each other a radical of formula —$N(R_3)R_4$, wherein $R_3$ and $R_4$ are, independently from each other, hydrogen; cyano; $C_1$-$C_8$alkyl which is unsubstituted or substituted by hydroxy, carboxy, cyano, —COON, —$H_2NC(NH)NH_2$—, —$CONH_2$ or phenyl, and wherein the $C_1$-$C_8$alkyl group is uninterrupted or interrupted by —O—; unsubstituted $C_5$-$C_7$cycloalkyl or $C_1$-$C_4$alkyl-substituted $C_5$-$C_7$cycloalkyl; or $R_3$ and $R_4$, together with the nitrogen atom linking them, form an unsubstituted morpholino, piperidine or pyrrolidine ring or a $C_1$-$C_4$alkyl-substituted morpholino, piperidine or pyrrolidine ring.

3. A storage-stable fluorescent whitener formulation according to claim 1 comprising 10 to 50% by weight, based on the total weight of the formulation, of at least one compound of formula (1).

4. A storage-stable fluorescent whitener formulation according to claim 1 wherein the anionic polysaccharide is selected from the group consisting of sodium alginate, carboxymethylated guar, carboxymethylcellulose, carboxymethyl-starch, carboxymethylated locust bean flour and xanthan gum.

5. A storage-stable fluorescent whitener formulation according to claim 1 comprising 0.05 to 0.5% by weight based on the total weight of the formulation, of at least one anionic polysaccharide.

6. A storage-stable fluorescent whitener formulation according to claim 1 wherein the electrolyte or the mixture of electrolytes are selected from the group consisting of alkali metal salts and salts of lower carboxylic acids.

7. A storage-stable fluorescent whitener formulation according to claim 1 comprising 0.5 to 20% by weight, based on the total weight of the formulation, of at least one electrolyte.

8. A storage-stable fluorescent whitener formulation according to claim 1 wherein the dispersant or the mixture of dispersants are selected from the group consisting of alkylbenzenesulfonates, alkyl or alkenyl ether-sulfonate salts, saturated or unsaturated fatty acids, alkyl or alkylene ether-carboxylic salts, sulfo-fatty acid salts or esters, phosphate esters, polyoxyethylene alkyl or alkenyl ethers, polyoxyethylene alkylvinyl ethers, polyoxypropylene alkyl or alkenyl ethers, polyoxybutylene alkyl or alkenyl ethers, higher fatty acid alkanolamides or alkylene oxide adducts, sucrose/fatty acid esters, fatty acid/glycol monoesters, alkylamine oxides and condensation products of aromatic sulfonic acids with formaldehyde and lignin-sulfonates.

9. A storage-stable fluorescent whitener formulation according to claim 1 comprising 0.1 to 20% by weight, based on the total weight of the formulation, of at least one dispersant.

10. A storage-stable fluorescent whitener formulation according to claim 1 comprising of at least one further fluorescent whitener of formula (2)

(2)

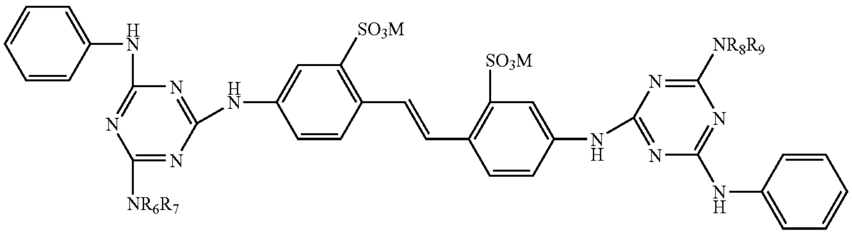

wherein $R_6$ and $R_8$, independently from each other, are hydrogen; unsubstituted $C_1$-$C_8$alkyl or substituted $C_1$-$C_8$alkyl, $R_7$ and $R_9$, independently from each other, are hydrogen; unsubstituted phenyl; unsubstituted $C_1$-$C_8$alkyl or substituted $C_1$-$C_8$alkyl, or $NR_6R_7$ and/or $NR_8R_9$ form a morpholino ring, and M is hydrogen or a cation.

11. A storage-stable fluorescent whitener formulation according to claim 10 wherein $R_6$ and $R_8$, independently from each other, are hydrogen; unsubstituted $C_1$-$C_2$alkyl or $C_1$-$C_4$alkyl, which is substituted by hydroxy or $C_1$-$C_4$alkoxy, $R_7$ and $R_9$, independently from each other, are unsubstituted phenyl; unsubstituted $C_1$-$C_2$alkyl or $C_1$-$C_4$alkyl, which is substituted by hydroxy or $C_1$-$C_4$alkoxy, or $NR_6R_7$ and/or $NR_8R_9$ form a morpholino ring, and M is an alkali metal atom.

12. A storage-stable fluorescent whitener formulation according to claim 1 comprising of at least one further fluorescent whitener of formula (3)

(3)

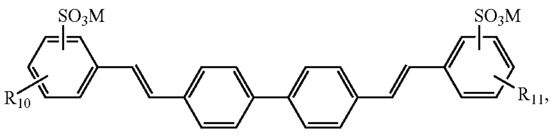

wherein $R_{10}$ and $R_{11}$, independently from each other, are hydrogen; $C_1$-$C_8$alkyl; $C_1$-$C_8$alkoxy or halogen, and M is hydrogen or a cation.

13. A storage-stable fluorescent whitener formulation according to claim 1 comprising 0 to 25% by weight of at least one further fluorescent whitener of formula (2)

(2)

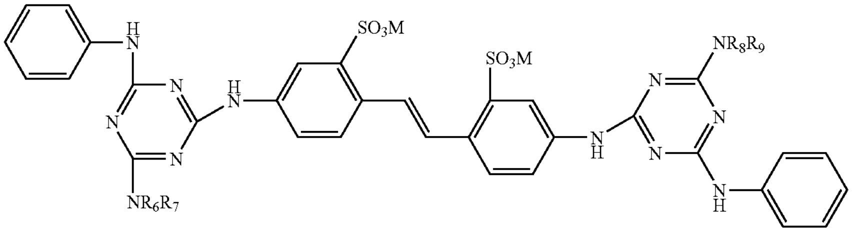

wherein $R_6$ and $R_8$, independently from each other, are hydrogen; unsubstituted $C_1$-$C_8$alkyl or substituted $C_1$-$C_8$alkyl, $R_7$ and $R_9$, independently from each other, are hydrogen; unsubstituted phenyl; unsubstituted $C_1$-$C_8$alkyl or substituted $C_1$-$C_8$alkyl, or $NR_6R_7$ and/or $NR_8R_9$ form a morpholino ring, and M is hydrogen or a cation and/or formula (3)

(3)

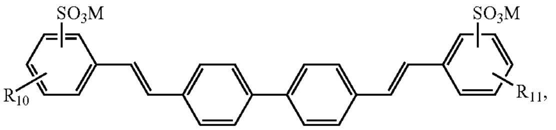

wherein $R_{10}$ and $R_{11}$, independently from each other, are hydrogen; $C_1$-$C_8$alkyl; $C_1$-$C_8$alkoxy or halogen, and M is hydrogen or a cation.

14. A storage-stable fluorescent whitener formulation according to claim 1 wherein optional components are selected from the group consisting of preservatives; Mg/Al silicates; odour improvers; perfuming agents; antifoam agents; builders; protective colloids; stabilizers; sequestering agents and antifreeze agents.

15. A storage-stable fluorescent whitener formulation according to claim 1 comprising 0.1 to 20% by weight based on the total weight of the formulation, of at least one optional component.

16. A process for the preparation of a storage-stable fluorescent whitener formulation according to claim 1, which comprises mixing the moist filter cake or the dry powder of the fluorescent whitening of formula (1) with least one anionic polysaccharide and water, and homogenizing the formulation.

17. A method for the preparation of a detergent composition, which comprises incorporating into said composition an effective whitening amount of a storage-stable fluorescent whitener formulation according to claim 1.

* * * * *